United States Patent
Flora et al.

(10) Patent No.: US 10,357,601 B1
(45) Date of Patent: Jul. 23, 2019

(54) METHOD AND APPARATUS FOR FIBRIN SHEATH DISRUPTION

(71) Applicant: Chrysalis Medical, Inc., Sunnyvale, CA (US)

(72) Inventors: Maurino G. Flora, San Jose, CA (US); David L. Black, Cameron, MT (US); Celso J. Bagaoisan, Union City, CA (US); Suresh Subraya Pai, Los Altos, CA (US); Marius C. Florescu, Omaha, NE (US)

(73) Assignees: CHRYSALIS MEDICAL, INC., Sunnyvale, CA (US); BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 210 days.

(21) Appl. No.: 15/257,468

(22) Filed: Sep. 6, 2016

(51) Int. Cl.
*A61M 1/36* (2006.01)
*A61M 25/00* (2006.01)

(52) U.S. Cl.
CPC ........ *A61M 1/3661* (2014.02); *A61M 1/3653* (2013.01); *A61M 25/0032* (2013.01); *A61M 25/0074* (2013.01); *A61M 2025/0019* (2013.01); *A61M 2025/0031* (2013.01); *A61M 2025/0034* (2013.01); *A61M 2025/0057* (2013.01)

(58) Field of Classification Search
CPC .............. A61M 1/3661; A61M 1/3653; A61M 25/0032; A61M 25/0074; A61M 2025/0034; A61M 2025/0031; A61M 2025/0019; A61M 2025/0057; A61M 1/3659; A61M 25/0026; A61M 25/003; A61M 25/0067; A61M 25/007; A61M 25/0071; A61M 2025/0035; A61M 2025/0037; A61M 2025/0063; A61M 2025/0079

See application file for complete search history.

(56) References Cited

U.S. PATENT DOCUMENTS

| | | | |
|---|---|---|---|
| 5,397,332 A | 3/1995 | Kammerer | |
| 5,752,934 A | 5/1998 | Campbell | |
| 6,270,477 B1 * | 8/2001 | Bagaoisan | ....... A61B 17/12045 604/102.01 |
| 6,692,466 B1 | 2/2004 | Chow | |
| 8,323,227 B2 | 12/2012 | Hamatake | |
| 8,608,688 B2 | 12/2013 | Jain | |
| 9,233,233 B2 | 1/2016 | Pruitt | |
| 9,238,119 B2 | 1/2016 | Thor | |

(Continued)

OTHER PUBLICATIONS

Percarpio, Robert, et al.; "Catheter-Related Sheaths (CRS): Pathophysiology and Treatment Strategies"; Chapter 33 in "Hemodialysis"; ISBN 978-953-51-0988-4; Feb. 27, 2013; http://dx.doi.org/10.5772/52944 [2016-0531].

(Continued)

*Primary Examiner* — Kevin C Sirmons
*Assistant Examiner* — Leah J Swanson
(74) *Attorney, Agent, or Firm* — Fernandez & Associates, LLP

(57) ABSTRACT

A hemodialysis catheter is disclosed for deploying in an artery or vein, comprising various means for disrupting, mechanically and/or chemo-mechanically, a fibrous sheath forming naturally outside of the catheter; optionally the disrupted fibrin sheath and/or thrombus is captured.

9 Claims, 3 Drawing Sheets

(56) References Cited

U.S. PATENT DOCUMENTS

| | | | |
|---|---|---|---|
| 2003/0171771 A1* | 9/2003 | Anderson | A61B 17/12172 |
| | | | 606/200 |
| 2005/0100580 A1* | 5/2005 | Osborne | A61L 29/085 |
| | | | 424/424 |
| 2005/0245900 A1* | 11/2005 | Ash | A61M 25/0017 |
| | | | 604/537 |
| 2009/0093748 A1 | 4/2009 | Patterson | |
| 2013/0324964 A1 | 12/2013 | Florescu | |
| 2016/0114124 A1 | 4/2016 | Gabriel | |

OTHER PUBLICATIONS

Ash, Stephen; "Advances in Tunneled Central Venous Catheters for Dialysis: Design and Performance"; Seminars in Dialysis—vol. 21, No. 6 Nov.-Dec. 2008. DOI: 10.1111/j. 1525-139x.2008.00494.x.

Bream, Jr., Peter R.; "Update on Insertion and Complications of Central Venous Catheters"; Seminars on Interventional Radiology; 2016; 33(01): 031-038; DOI:10.1055/s-0036-1572547.

Faintuch, Salao, et al.; "Malfunction of Dialysis Catheters:"; Tech Vasc Interventional Rad 11:195-200, 2008; doi:10.1053/j.tvir.2008.09.008.

Bills, Matthew; "A Deeper Look into Lumens"; http://www.mddionline.com/print/7611; Jan. 27, 2011.

Laduca, Robert; "Extruding the Best Out of Multilumen Tubing"; http://www.dukeempirical.com; Mar. 3, 2014.

* cited by examiner

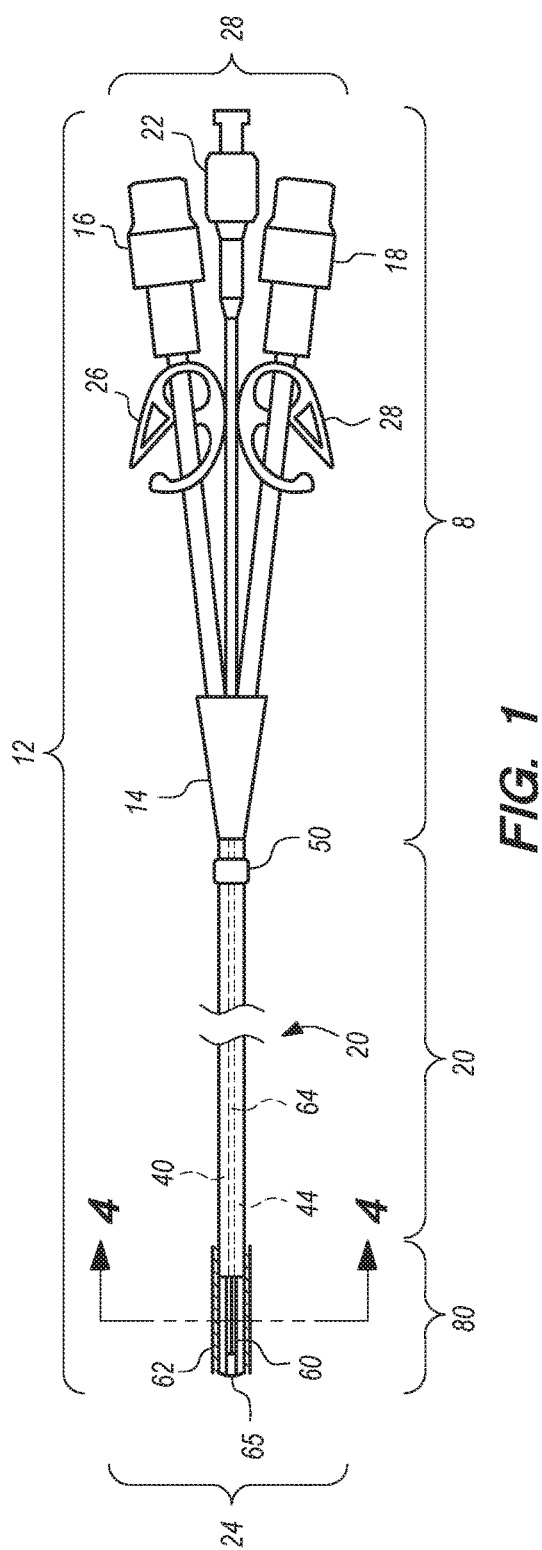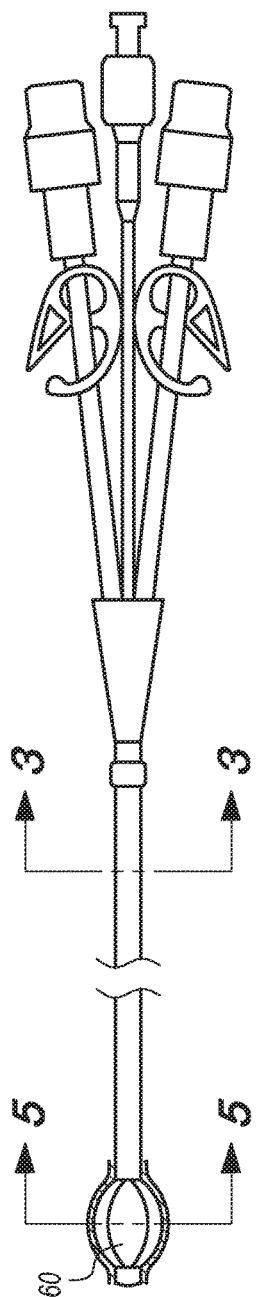
FIG. 1
FIG. 2

METHOD AND APPARATUS FOR FIBRIN SHEATH DISRUPTION

CROSS-REFERENCE TO RELATED APPLICATION

This application contains material from U.S. application Ser. No. 13/993,004, now published as 2013/0324964 and the subject matter thereof is incorporated herein by reference in its entirety.

BACKGROUND OF THE INVENTION

Field of Invention

The instant invention discloses a hemodialysis catheter, and comparable devices deployed or implanted in an artery or vein, comprising various means for disrupting mechanically and/or chemo-mechanically a fibrous sheath forming naturally outside of the catheter; optionally the disrupted fibrin sheath and/or thrombus is captured.

Background Material

The average diameter of a coronary artery is 4.6 mm. The instant invention is typically placed within the Superior Vena Cava. Hemodialysis requires a large vessel and the SVC is the vessel of choice. The lumens of the instant invention must be larger than 4.6 mm in diameter; the size of the coronary arteries are such that the instant invention is not appropriate for arteries without serious modification. The superior vena cava (SVC) is the superior of the two venae cavae, the great venous trunks that return deoxygenated blood from the systemic circulation to the right atrium of the heart. The SVC is a large-diameter, typically between about 18 to 24 mm, yet a short vein that receives venous return from the upper half of the body, above the diaphragm. Venous return from the lower half, below the diaphragm, flows through the inferior vena cava. The SVC is located in the anterior right superior mediastinum. It is the typical site of central venous access (CVA) via a central venous catheter or a peripherally inserted central catheter. Mentions of "the cava" without further specification usually refer to the SVC.

In the instant invention the lumens may encompass a balloon or other separation device. The lumens form a barrier between a separation device and a patient's blood flow. A standard angioplasty balloon is made of folded material. The folds of the material provide a surface that is thrombogenic. The patient would be at an increased risk of clot. Beyond the structural difference, the added feature shows that the device can be used for implanted, long-term hemodialysis.

Catheter occlusion is the most common noninfectious complication in the long-term use of central venous access devices (CVADs), occurring in up to 25% of catheters. Fibrin formation is a natural process that may occur soon after insertion of a device or develop at any time during the course of IV therapy. The four main types of thrombotic CVAD occlusions are intraluminal thrombus, fibrin tail, mural thrombus, and fibrin sheath. All catheters, when introduced into the body, become covered with plasma proteins and fibrin. This is the body's natural attempt to protect itself against a foreign body. The fibrin starts to form a layer around the outside of the catheter within minutes of insertion, starting at either the line entry site or where the tip contacts the vein. The concentration of proteins on the catheter surface equals the concentration in the bloodstream within 5 minutes of insertion, and a 1-mm thick layer of platelets and white blood cells adhere to these proteins within 24 hours. These absorbed blood components can allow the binding and colonization of bacteria, which can increase fibrin formation and may activate the clotting mechanism. Of interest for the instant invention is when a lumen, or ports, of the catheter is encased with fibrin sheath thereby preventing flushing of a catheter's input or output lines while a catheter is aspirating blood or conveying medicaments to the body or performing dialysis. Hemodialysis, commonly called kidney dialysis or simply dialysis, is a process of purifying the blood of one suffering from acute renal failure. Hemodialysis is a method that is used to achieve the extracorporeal removal of waste products such as creatinine, urea and free water from the blood when the kidneys are in a state of renal failure or diminished capacity. An alternative method for extracorporeal separation of blood components such as plasma or cells is apheresis.

Hemodialysis is typically done 2-3 times a week and allows patients to survive and lead almost normal lives. More than half of the patients starting hemodialysis use a tunneled hemodialysis catheter as a vascular access. Every year in the United States, approximately 500,000 hemodialysis catheter procedures are performed, half of which involve placement or exchange of a hemodialysis catheter. Similarly, there are approximately 2 million hemodialysis procedures performed annually worldwide, most of which involve placement or exchange of the hemodialysis catheter. While a variety of hemodialysis catheters are available, conventional hemodialysis catheters are comprised of two tubes or lumens, each with a lumen aperture disposed at its distal end. One tube carries or transports a patient's blood to be cleaned, while the other lumen returns cleaned blood to the patient.

One of the most common catheter failures for long-term dialysis catheters is the formation of a fibrin sheath blocking the lumen apertures in a catheter; fibrin sheath forms an occlusion and/or blockage; an occlusion and/or blockage usually starts developing upon catheter insertion. The term "fibrin sheath" is misleading since a sheath can be composed of thrombus, endothelial cells and collagen, depending on the duration of the catheter placement. A fibrin sheath may cover the inlet and outlet holes of a hemodialysis catheter acting as a one-way valve. Even partial encasement can prevent flow rates required for satisfactory hemodialysis. Fibrous sheath formation is especially problematic for implanted catheters that are designed to stay implanted for months at a time. Fibrous sheaths form around all hemodialysis catheters, causing dysfunction in a significant number of them. In fact, this type of catheter dysfunction accounts for nearly half of all procedures involving the exchange of implanted hemodialysis catheters. In these circumstances, the hemodialysis catheter is removed and the fibrous sheath is obliterated by external means or the catheter is discarded. Thereafter, a new catheter is placed inside the patient. This procedure is risky and is expensive because it is done under sterile conditions in fluoroscopy (X-ray)-equipped procedure rooms by specially trained doctors and nurses with the patient under conscious sedation.

The following citations contain material related to the instant invention; all are incorporated herein in their entirety by reference; U.S. Pat. Nos. 8,608,688; 5,397,332; 9,233,233; 9,238,119; 5,752,934; 6,692,466; 8,323,227; U.S.2016/0114124; U.S.2009/0093748; PERCARPIO, ROBERT, et al.; "Catheter-Related Sheaths (CRS): Pathophysiology and Treatment Strategies"; Chapter 33 in "Hemodialysis"; ISBN 978-953-51-0988-4; Feb. 27, 2013; http://dx.doi.org/

10.5772/52944 [2016-0531]; ASH, STEPHEN; "Advances in Tunneled Central Venous Catheters for Dialysis: Design and Performance"; Seminars in Dialysis—Vol. 21, No. 6 November-December, 2008. DOI: 10.1111/j. 1525-139x.2008.00494.x;

BREAM, JR., PETER R.; "Update on Insertion and Complications of Central Venous Catheters"; Seminars on Interventional Radiology; 2016; 33(01): 031-038; DOI: 10.1055/s-0036-1572547; FAINTUCH, SALAO, et al.; "Malfunction of Dialysis Catheters:"; Tech Vasc Interventional Rad 11:195-200, 2008; doi:10.1053/j.tvir.2008.09.008; BILLS, MATTHEW; "A Deeper Look into Lumens"; http://www.mddionline.com/print/7611; Jan. 27, 2011; LADUCA, ROBERT; "Extruding the Best Out of Multilumen Tubing"; http://www.dukeempirical.com; Mar. 3, 2014.

U.S. Pat. No. 8,608,688, entitled, "Catheter Apparatus", assigned to Barts and the London NHS Trust discloses a catheter apparatus comprising an actuator controllable to move the distal ends of the lumens relative to each other. Accordingly, the separation of the guidewires can be controlled, enabling probing by the guidewires of different areas of an occlusion in a blood vessel, such as a chronic total occlusion. However, the invention does not disclose an inflatable balloon, as well as a protraction and retraction mechanism for the capture and recovery of the fibrin sheath. Moreover, U.S. Pat. No. 8,608,688 does not disclose a thin, smooth transparent, flexible medical grade material protecting the entrance and exit lumens of the instant invention and acting as a sleeve around the lumens and displacement device as disclosed herein.

BRIEF SUMMARY OF THE INVENTION

Catheter-related sheath (CRS) formation, also referred to as "fibrin sheath" is a well-documented, natural phenomenon that occurs between a catheter, vein wall and blood elements. The incidence of central venous fibrin sheath formation is reported to occur in 42%-100% of central venous catheters. The sheaths can be asymptomatic or result in a number of complications including withdrawal occlusion, medication extravasation, thrombosis, infection and, in rare cases, pulmonary embolism. Repeat catheter removal and replacement, or loss of an access route is frequently the end result of catheter related sheath formation.

Fibrous tissue naturally accumulates on the surfaces of implanted hemodialysis catheters over time. This accumulation of fibrous tissue can eventually lead to occlusion of openings in the catheter through which blood flows into and out of the patient. The most common manifestation of fibrin sheath is catheter dysfunction. This interrupts the patient's medical therapy, may require intervention ranging from thrombolytic infusion to catheter removal or exchange, and may have long lasting implications such as loss of specific venous access locations. Extravasation of fluids or intravenous medication is a less common but certainly significant complication that can result in tissue loss and necrosis. Thrombus that forms on the fibrin sheath or the fibrin sheath itself can on rare occasion become dislodged and embolize to the pulmonary circulation. Finally, there have been reports that the presence of the sheath is a risk factor for catheter-related bacteremia and infection.

This occlusion typically requires the catheter be removed and replaced from the patient. Once the catheter is removed, an angioplasty balloon is typically used for the disruption of the fibrous tissue followed by a replacement of a new catheter. The procedure of removing the catheter, disrupting the fibrous tissue, and replacing the previous catheter with a new catheter is expensive, strenuous and physically taxing on the patient. The present invention describes embodiments of an apparatus and method in which a catheter itself is utilized to break or disrupt fibrin sheath and, in cases where a fibrin capture element is used, capture at least a portion of the occluding fibrous sheath. As a result, the accumulated fibrous sheath can be disrupted without removing the catheter. Fibrous tissue formation is a problem that can impact all catheters. Although not shown in FIG. 1, the materials encased can be any foreign material or naturally formed material such as a fibrin sheath. The device can be a hemodialysis catheter or any implanted device inside the anatomy. The implantation site can be close to the heart, kidneys or any location inside the body. The embodiment can be used for human and or any animals requiring disruption and/or break encasement(s). The disruption and/or break will result in an improved functionality as for example, improved blood flow during hemodialysis as well as improved contact points for electrical and/or mechanical functionality.

While the present disclosure is preferably used in catheters with exit ports that are close to each other, one of ordinary skill in the art would understand that the present disclosure has broad applicability beyond use in hemodialysis catheters. With reference now to the drawings, and in particular to FIGS. 1 through 9 thereof, an apparatus and method for the disruption and capture of this catheter-encased fibrin sheath is hereby illustrated and described.

In some embodiment of the instant invention a means for chemically disrupting the encased sheath, in addition to delivering mechanical disruption, is disclosed. In some embodiments, a flexible sleeve may be coated, impregnated, or embedded with sheath-retarding or disrupting compositions, such as silicone, hydrophilic or hydrophobic based coatings, collagenase; other sheath-disrupting compositions may be used to impregnate, embed, or coat the displacing sleeve. Collagenases are enzymes that break the peptide bonds in collagen. Sheath-retarding compounds include those on which it is more difficult for fibrin to attach to; a silicon impregnated surface wherein the silicon is slowly dissolved by the basic pH of the blood stream is one example. In some embodiments a flexible sleeve may be of a stent-like wire mesh; alternatively, a flexible sleeve may be a porous structure further composed of a plurality of traversable pores enabling a controlled release of collagenase, or any of sheath disrupting/retardant compositions. In another embodiment of the instant invention a means for chemically disrupting the encased sheath by conveyance of fibrin sheath medicaments to dissolve or weaken or break up the sheath is disclosed. The medicaments can be injected through, optionally, a fourth lumen. Extruded tubular channels and lumens as described herein are commercially available from Duke Empirical of Santa Cruz, Calif., among others.

One object of the instant invention is to provide an expandable fibrin capture element positioned distal to the $3^{rd}$ portion. A fibrin capture element may be, optionally, a filter or wire umbrella mechanism; optionally comprising wire or suture material or surgical mesh or combinations thereof; optionally comprising a NiTi (Nitinol) portion; optionally, comprising shape memory polymers (SMPs); optionally, comprising a copolymer based material portion that is retractably deployed and conveyed through a lumen of the tubular member; the function of this retractable umbrella is to catch or ensnare fibrin sheath particles that may detach or break loose from the catheter during a fibrin sheath breaking procedure.

Optionally, a catheter of the instant invention comprises pivotally opposable members of an expandable sheath fibrin capture element further comprising a plurality of pliably opposable arms engaged to a longitudinal member slidably disposed within a channel and operably coupled to a, manual actuator at a proximal end of a tubular apparatus. The actuator causes displacement of pliably opposable arms and pivotally opposable members, causing either protraction or retraction of the expandable sheath fibrin capture element out of the distal port of a lumen; this step is done just prior to displacement of the lumens resulting in disruption and/or displacement of a fibrin sheath resulting in capture of just disrupted fibrin sheath by the expanded fibrin capture element mechanism. In another aspect of the invention, an expandable fibrin-sheath fibrin capture element is disposed in a collapsed state over a displacing sleeve. Upon expansion of the displacing sleeve by the expansion tube or opposable arms, the mesh fibrin capture element expands into an open state, situated in a distal portion of the sleeve. Subsequent to capturing the disrupted fibrin sheath during removal of the catheter, the fibrin capture element may re-collapse by a distal end member of the catheter sliding down to collapse the fibrin capture element. In yet other aspects, the sleeve-coupled fibrin capture element may collapse by opposable arms coupled to a longitudinal member engaging with an actuator.

In one embodiment of the instant invention, a means for displacement mechanism such as a balloon, mechanical wedge, insert molded wire, preformed wire configuration, is placed at the distal end of the catheter via an appropriate method. Aspects and advantages of this invention may be realized in other applications, aside from the intended application. Other applications may include coronary artery surgery, various endoscopic procedures, ureterscopy, laser lithotripsy, and percutaneous nephrolithotomy.

Other aspects and advantages of the invention will be apparent from the following description and the appended claims. It is to be understood that the foregoing general description and the following detailed description are exemplary and explanatory only, and are not necessarily restrictive of the disclosure. The accompanying drawings, which are incorporated in and constitute a part of the specification, illustrate subject matter of the disclosure and together with the general description, serve to explain the principles of the present disclosure. The disclosure will be understood by those skilled in the art from the following detailed description and drawings.

BRIEF DESCRIPTION OF THE DRAWINGS

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which:

FIG. 1 is a schematic view of a hemodialysis catheter according to an aspect of the invention.

FIG. 2 is a schematic view of a hemodialysis catheter with an expanded displacement mechanism according to an aspect of the invention.

DETAILED DESCRIPTION OF THE INVENTION

Figure 3:
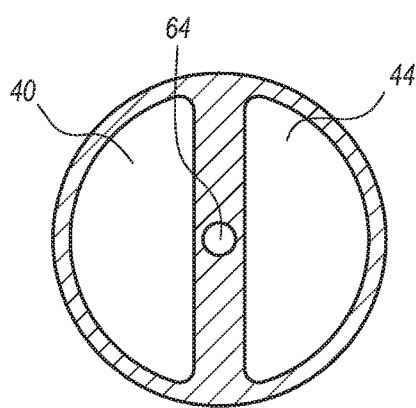
FIG. 3 is a first schematic cross section view of the second portion of a hemodialysis catheter according to an aspect of the invention.
Figure 5:
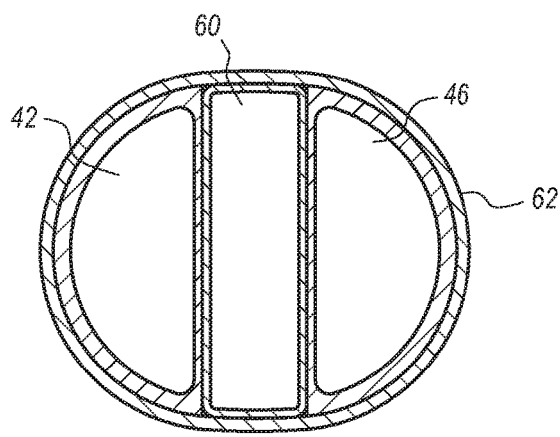
FIG. 5 is a third schematic cross section view of the third portion of a hemodialysis catheter in an expanded state according to an aspect of the invention.
Figure 6:
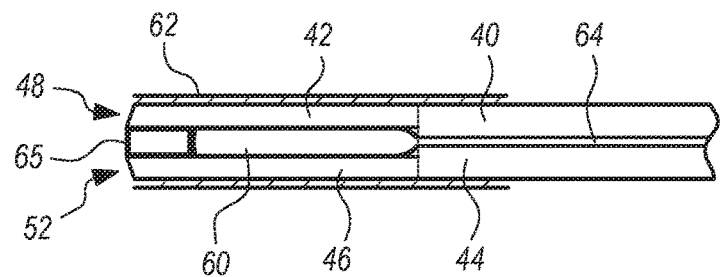
FIG. 6 is a fourth schematic cross section view of the distal end of the third portion of a hemodialysis catheter according to an aspect of the invention.
Figure 7:
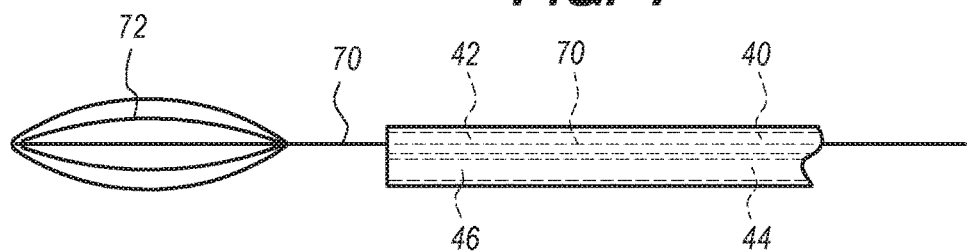
FIG. 7 is a cross section view of an extended, expanded wire mesh fibrin capture element according to an aspect of the invention.
Figure 8:
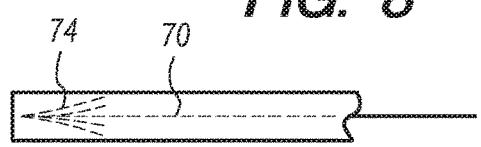
FIG. 8 is a cross section view of an not-extended fibrin capture element according to an aspect of the invention.
Figure 9:
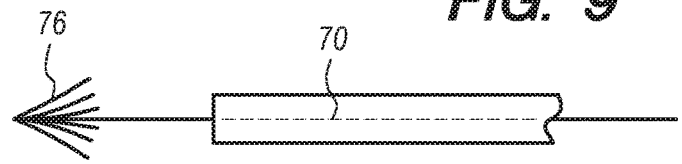
FIG. 9 is a cross section view of an extended, expanded wire umbrella fibrin capture element according to an aspect of the invention.

As shown in FIG. 1, the present invention discloses a dialysis catheter comprising a tubular apparatus 12 comprising proximal end 28 and distal end 24; first portion 8 comprises a hub 14, a first Luer 16, optionally functioning as an inlet for blood returning to a vein, a second Luer 18, optionally functioning as an exit for blood leaving a vein, third Luer 22, first clamp 26, and second clamp 28, wherein the hub attaches the first portion to the second portion 20. The second portion comprises an extruded tubular section comprising Dacron cuff 50, first, second and third channels, 40, 44, and 64; the third channel located between the first and second channels is shown in FIG. 3. In the third portion 80 channel 40 becomes separated lumen 42 and channel 44 becomes separated lumen 46; channel 64 is attached to means for displacement 60. As shown in FIG. 6, lumen 42 has a first opening port 48 located at its distal end; optionally, functioning as an entrance port for blood returning to a vein; lumen 46 has open port 52 at its distal end; optionally, functioning as an exit port for blood exiting a vein; plug 65 is placed between lumens 42 and 46, covering the end of means for displacement 60. Flexible sleeve 62 covers the third portion 80; Flexible sleeve 62 is typically a thin, smooth transparent, flexible medical grade material functioning as a sleeve around the lumens and displacement device protecting the entrance and exit lumens. FIGS. 2 and 5 show apparatus 12 with means for displacement 60 in an expanded state. Optionally, channels 40 or 44 and lumens 42 and 46 may be used for positioning an expandable fibrin capture element mechanism wire 70 into a patients vein for purposes of catching fibrin sheath material that is dislodged or broken off from around the distal end of the catheter from the action of the means for displacement; wire 70 is attached to optional fibrin capture element mechanisms 72, 74 or 76. FIG. 7 shows expanded wire mesh catch mechanism 72 external to apparatus 12, in position to catch dislodged fibrin sheath. FIG. 8 shows catch mechanism 74 not yet extended and still in lumen 42 or 46. FIG. 9 shows wire umbrella fibrin capture element 76 external to apparatus 12, expanded and in position to entrain fibrin material. Fibrin capture element mechanisms 72, 74 and 76 are exemplary embodiments of possible ways to ensnare pieces of fibrin dislodged from a hemodialysis catheter.

Optionally, different connectors may be used in place of the Luer fittings; particularly, Luer 22 when it provides access and control of means for displacement 60. As used herein means for displacement may be chosen from a group consisting of balloon, mechanical wedge, pulley, insert molded wire, preformed wire configuration, and/or mechanical screw to widen the distance between lumens 42 and 46 such that the displacement is at least about 3 mm and up to as much as 12 mm. Lumens 42 and 46 are pinned in place at their respective ends by channels 40 and 44 at their proximal end and by plug 65 at their distal end; the 3 mm separation will occur between the distal end and the proximal end based on which means for displacement is chosen. Please note the all means for displacement are reversible such that the lumen displacement can be returned to zero. After a fibrin capture element mechanism is introduced flexible sleeve 62 on which the fibrin collects is expanded with means for displacement 60 causing the fibrin sheath to be disrupted or broken and displaced. Optionally, the expandable fibrin capture element mechanism wire 70 is in place with expanded surgical mesh 72 or wire umbrella 76. In the embodiments where the catch mechanism is used Luer 16 or 18 is replaced with a mechanical device suitable for the particular catch mechanism used; for instance, a catch actuator placed in the first portion of the tubular apparatus, whereby activation of the catch actuator causes the expandable catch mechanism to extend out of the first or second lumens and expand into an open state operable for collection of displaced fibrin sheath. In some embodiments third portion 80 is considered to be an "atraumatic tip".

Figure 4:
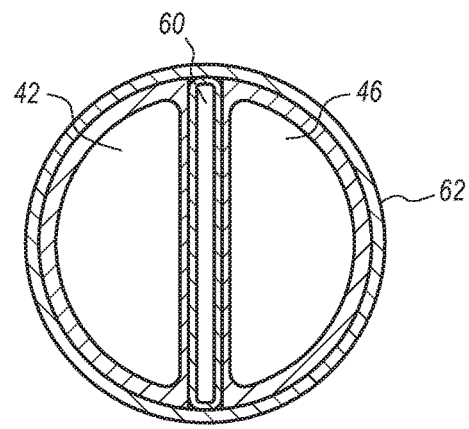
FIG. 4 is a second schematic cross section view of the third portion of a hemodialysis catheter according to an aspect of the invention.

In some embodiments a balloon 60 is entrained through Luer 22 and put into non-inflated position between lumens 42 and 46 as shown in FIG. 4; FIG. 5 shows an expanded state of balloon 60 wherein the cross section of balloon 60 is at least 3 mm greater than in FIG. 4.

In one embodiment of the invention surgical mesh is a sterile, thin, flexible, collapsible, elastomeric laminate mesh composed on an oxidized, regenerated cellulose fabric for example, PROCEED™ Surgical mesh, Sepramesh™ IP Composite, PHYSIOMESH™ may be used.

One embodiment of the sleeve-coupled, fibrin capture element may include expansion of the displacing sleeve via the deployment tube or line as a means of expanding the fibrin capture element coupled and collapsed over the sleeve. After capturing of the fibrin sheath and any other occluding debris, the sleeve-coupled fibrin capture element may close back into the collapsed state by an actuating arm engaged to the pivotally opposable members of the fibrin capture element, or by a distal end portion of the tubular member sliding down to cover and re-collapse the sleeve-coupled fibrin capture element.

One embodiment of the invention provides an expandable fibrin capture element 72 or 76, disposed through channel 40 and lumen 42, or through channel 44 and lumen 46, that is rotatable so that the fibrin capture element can capture a wider area of disrupted fibrin sheath. The fibrin capture element 72 or 76 is rotatable when protracted to allow the angular orientation of the surgical mesh field to be adjusted. In a further embodiment of the invention, a fibrin capture element 72 or 76 includes an expandable surgical mesh field, which is adjustable depending on the debris field. The protraction and retraction of the fibrin capture element 72 or 76 as described above is actuated using suitable mechanical forces via an actuators. Each of the actuators may be located external to the patient or integrated into the catheter device and placed inside the patient. The protraction and retraction of the fibrin capture element 72 or 76 as described above, as well as any or all displacement forces, may be actuated using suitable electro-mechanical, mechanical, electromagnetic, or any other force via the actuators. The actuation may also be manually carried out by a caregiver or carried out using a motor in some embodiments.

In an alternative embodiment of the invention, an adhesive-coated surgical wire mesh, such as 72 or 76, may be used as the fibrin capture element. The disrupted fibrin sheath sticks to the surgical mesh; the mesh plus fibrin is removed simultaneously through its lumen and channel. Optionally, a fibrin capture element comprising surgical wire or surgical mesh may be employed to retrieve disrupted fibrin sheath, any dislodged foreign matter, thrombus, calcified debris and/or combinations thereof.

In an embodiment we disclose a hemodialysis catheter apparatus 12 operable to disrupt an external fibrin sheath comprising a tubular apparatus comprising a first portion 8, extruded second portion 20 and partially extruded third portion 80 wherein the first portion is external to a patient and its distal region is connected to the extruded second portion through a hub 14 and the second portion's proximal region is external to a patient and the second portion's distal portion is internal to the patient and the proximal end of the third portion is connected to the distal end of the second portion; first 40, second 44 and third 64 channels disposed within the second portion of the tubular apparatus; a first 42 and second lumen 46 and displacement mechanism 60 disposed within the third portion of the tubular apparatus wherein the first lumen is connected to the first channel and the second lumen is connected to the second channel and the displacement mechanism separates the first lumen from the second lumen and is connected to the third channel wherein the first channel comprises an exit port 48 and the second channel comprises an entrance port 52 at their distal ends; a plug 65 located on the distal portion of the third portion wherein the first lumen and the second lumen are separated by the plug such that there is no flow from the first or second lumen to the other lumen; and a flexible sleeve 62 overcladding the third portion of the tubular apparatus wherein the means for displacement 60 is operable to displace a portion of the first lumen from a portion of the second lumen by more than 3 mm such that at least a portion of an external fibrin sheath is disrupted. In an alternative embodiment channel 46 comprises an entrance port 54, not shown, at the proximal end, adjacent channel 44; optionally entrance port 52 may or may not be present. Alternatively, channel 42 comprises an exit port 49, not shown, at the proximal end, adjacent channel 40; optionally entrance port 48 may or may not be present. In some embodiments means for displacement comprises an actuator at a proximal end of the first portion of tubular apparatus in communication via the third channel with a means for displacement located in the third portion of the tubular apparatus causing. In some embodiments a catheter of the instant invention comprises a flexible sleeve comprising one or more sheath disrupting compositions; alternatively, a flexible sleeve comprises a plurality of traversable pores operable to achieve a controlled release of one or more sheath disrupting compositions.

In some embodiments a catheter of the instant invention comprises an expandable fibrin capture element mechanism disposed within the first or second lumens and engaged to a catch actuator wire 70 and a catch actuator, not shown, in the first portion of the tubular apparatus, whereby activation of the catch actuator causes the expandable fibrin capture element mechanism to extend out of the first or second lumens and expand into an open state operable for collection of displaced fibrin sheath as schematically shown in FIGS. 7, 8 and 9. Expansion and disruption of a fibrin sheath occurs after the extension of the fibrin capture element; this is done when no hemodialysis is occurring so that channels 40 and 44 and lumens 42 and 46 are not in use for blood flow.

In some embodiments a hemodialysis catheter of the instant invention comprises a tubular apparatus comprising a distal portion and a proximal portion and first, second and third channels; a means for displacement disposed within the distal portion of the tubular apparatus between the first channel and the second channel and connected to the third channel wherein the first channel is not in contact with the second channel and wherein the first channel comprises an exit port and the second channel comprises an entrance port at the end or beginning of the distal portion; a flexible sleeve over-cladding the distal portion of the tubular apparatus wherein the means for displacement is operable to displace the first channel from the second channel by more than 3 mm; and an expandable fibrin capture element comprising surgical mesh or wire disposed within the first or second channels and engaged to a catch actuator in the proximal portion of the tubular apparatus through the first or second channels, whereby activation of the catch actuator causes the expandable sheath catch mechanism to extend out of the first or second lumens and expand into an open state operable for collection of displaced fibrin sheath. It is noted that the first and second channels are held in their respective positions by the flexible sleeve; the means for displacement separates the two channels and displaces them apart from each other in their middle regions. In an alternative embodiment second channel comprises an entrance port where the proximal portion of the flexible sleeve ends. Alternatively, first channel comprises an exit port where the proximal portion of the flexible sleeve ends. In some embodiments a flexible sleeve is further coated with one or more sheath disrupting compositions; optionally, a flexible sleeve is further composed of a plurality of traversable pores enabling a controlled release of collagenase, or any one of sheath disrupting composition.

A method of disrupting and capturing fibrin sheath on a catheter; the method comprising the steps of; extending an expandable fibrin capture element outside of a lumen housed within a tubular apparatus; expanding the fibrin capture element; expanding a distal portion of the catheter by at least 3 mm so that the fibrin sheath is disrupted and detaches from the catheter; and capturing the disrupted fibrin sheath in the fibrin capture element.

The instant invention disclosed herein shares some similarities with the cited U.S.2013/0324964 application. However there are several distinctive differences not obvious from U.S.2013/0324964 and the published art. First separating the two primary lumens 42 and 46 from each other and then encasing them in a flexible sleeve such that their motion is severely restricted is not found or suggested in U.S.2013/0324964. The fact that the distal ends of the lumens are attached to a plug means that actions such as those shown in FIGS. 3B, 3C, 4, 5 and 6 of U.S.2013/0324964 are not possible with the instant invention; the instant invention relies on displacing the "middle" region of the lumens from each other; not the freely moving distal ends of the lumen. Thirdly, the expandable and retractable fibrin capture element for capturing displaced fibrin is not found in the published literature, including U.S.2013/0324964.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the invention.

Unless otherwise defined, all terms used in disclosing embodiments of the invention, including technical and scientific terms, have the same meaning as commonly understood by one of ordinary skill in the art to which this invention belongs, and are not necessarily limited to the specific definitions known at the time of the present invention being described. Accordingly, these terms can include equivalent terms that are created after such time. It will be further understood that terms, such as those defined in commonly used dictionaries, should be interpreted as having a meaning that is consistent with their meaning in the present specification and in the context of the relevant art and will not be interpreted in an idealized or overly formal sense unless expressly so defined herein. All publications, patent applications, patents, and other references mentioned herein are incorporated by reference in their entirety.

In the following description, for purposes of explanation, numerous specific details are set forth in order to provide a thorough understanding of the invention. It will be apparent, however, to one skilled in the art that the invention can be practiced without some specific details. Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments. Although a few exemplary embodiments of the present disclosure have been shown and described, the present disclosure is not limited to the described exemplary embodiments. Instead, it would be appreciated by those skilled in the art that changes may be made to these exemplary embodiments without departing from the principles and spirit of the present disclosure, the scope of which is defined by the claims and their equivalents.

It will be understood that when a layer is referred to as being "on top of" another layer, it can be directly on the other layer or intervening layers may also be present. In contrast, when a layer is referred to as "contacting" another layer, there are no intervening layers present. Similarly, it will be understood that when a layer is referred to as being "below" another layer, it can be directly under the other layer or intervening layers may also be present.

It will also be understood that, although the terms first, second, etc. may be used herein to describe various elements, these elements should not be limited by these terms. These terms are only used to distinguish one element from another. For example, a first layer could be termed a second layer, and, similarly, a second layer could be termed a first layer, without departing from the scope of the present invention.

We claim:

1. A hemodialysis catheter apparatus operable to disrupt an external fibrin sheath comprising: a tubular apparatus comprising a first portion, extruded second portion and partially extruded third portion, each of the three portions comprising a distal region and a proximal region, wherein the first portion is configured to be external to a patient, and the first portion's distal region is connected to the extruded second portion through a hub, and the second portion's proximal region is configured to be external to a patient, and the second portion's distal region is configured to be internal to the patient, and the proximal region of the partially extruded third portion is connected to the distal region of the second portion; first, second and third channels disposed within the second portion of the tubular apparatus; a first and second lumen, each lumen comprising a proximal, a middle and a distal section, and means for displacement disposed within the third portion of the tubular apparatus wherein the first lumen, at its proximal section, is connected to the first channel and the second lumen, at its proximal section, is connected to the second channel and the means for displacement separates the first lumen from the second lumen and is connected to the third channel wherein the first channel comprises an exit port at a distal end of the first channel and the second channel comprises an entrance port at a distal end of the second channel; a plug located on the distal region of the third portion wherein the distal section of the first lumen and the distal section of the second lumen are separated by and pinned in place by the plug; and a flexible sleeve over-cladding the entirety of the third portion of the tubular apparatus including the first and second lumens wherein the means for displacement is operable to displace only the middle section of the first lumen from only the middle section of the second lumen by more than 3 mm such that at least a portion of an external fibrin sheath is disrupted.

2. The apparatus of claim 1 wherein the means for displacement comprises an actuator at a proximal end of the first portion of tubular apparatus in communication via the third channel with the means for displacement located in the third portion of the tubular apparatus.

3. The catheter of claim 1, wherein the flexible sleeve is substantially a thin, smooth, transparent, flexible medical grade material.

4. The catheter of claim 3 wherein the flexible sleeve comprises a plurality of traversable pores.

5. The catheter of claim 1 further comprising: an expandable fibrin capture element disposed within the first or second lumen and engaged to a catch actuator in the first portion of the tubular apparatus, whereby activation of the catch actuator causes the expandable fibrin capture element to extend out of the first or second lumen and expand into an open state operable for collection of displaced fibrin sheath.

6. A catheter comprising: a tubular apparatus comprising a distal portion and a proximal portion and first, second and third channels, each of the three channels comprising a distal region and a proximal region; and a means for displacement disposed within the distal portion of the tubular apparatus separating the first channel from the second channel and connected to the third channel wherein the first channel is not in contact with the second channel and wherein the first channel connects to a first lumen comprising an exit port at an end of the distal portion and the second channel connects to a second lumen comprising an entrance port at the end of the distal portion; a flexible sleeve over-cladding the entirety of the distal portion of the tubular apparatus wherein the means for displacement is operable to displace a middle portion of the first channel from a middle portion of the second channel by more than 3 mm; and an expandable fibrin capture element comprising surgical mesh or wire disposed within the first or second channel and engaged to a catch actuator in the proximal portion of the tubular apparatus through the first or second channel, whereby activation of the catch actuator causes the expandable fibrin capture element to extend out of the first or second lumen and expand into an open state operable for collection of displaced fibrin sheath.

7. The catheter of claim 6, wherein the flexible sleeve is substantially a thin, smooth, transparent, flexible medical grade material.

8. The catheter of claim 7, wherein the flexible sleeve is further composed of a plurality of traversable pores enabling a controlled release of collagenase, or any sheath disrupting compositions.

9. A method of disrupting fibrin sheath while performing hemodialysis, coronary artery surgery, endoscopic procedures, ureterscopy, laser lithotripsy, or percutaneous nephrolithotomy when a catheter is required, the method comprising the steps of: inserting a catheter comprising a tubular apparatus comprising a first portion, extruded second portion and partially extruded third portion, each of the three portions comprising a distal region and a proximal region, wherein the first portion is configured to be external to a patient, and the first portion's distal region is connected to the extruded second portion through a hub, and the second portion's proximal region is configured to be external to a patient, and the second portion's distal region is configured to be internal to the patient, and the proximal region of the partially extruded third portion is connected to the distal region of the second portion; first, second and third channels disposed within the second portion of the tubular apparatus; a first and second lumen, each lumen comprising a proximal, a middle and a distal section, and means for displacement disposed within the third portion of the tubular apparatus wherein the first lumen, at its proximal section, is connected to the first channel and the second lumen, at its proximal section, is connected to the second channel and the means for displacement separates the first lumen from the second lumen and is connected to the third channel wherein the first channel comprises an exit port at a distal end of the first channel and the second channel comprises an entrance port at a distal end of the first channel; a plug located on the distal region of the third portion wherein the distal section of the first lumen and the distal section of the second lumen are separated by and pinned in place by the plug; and a flexible sleeve over-cladding the entirety of the third portion of the tubular apparatus including the first and second lumens wherein the means for displacement is operable to displace only a middle section of the first lumen from only a middle section of the second lumen by more than 3 mm; displacing the first and second lumens of the catheter by at least 3 mm such that the fibrin sheath is disrupted and detaches from the catheter.

* * * * *